(12) United States Patent
Ekström et al.

(10) Patent No.: US 7,604,773 B2
(45) Date of Patent: Oct. 20, 2009

(54) METHOD OF STERILISING A PACKAGING MATERIAL BY MEANS OF A STERILISING AGENT IN LIQUID FORM

(75) Inventors: Jan-Erik Ekström, Höör (SE); Lars Sickert, Lund (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 323 days.

(21) Appl. No.: 10/493,201

(22) PCT Filed: Nov. 21, 2002

(86) PCT No.: PCT/SE02/02113

§ 371 (c)(1),
(2), (4) Date: Apr. 21, 2004

(87) PCT Pub. No.: WO03/045447

PCT Pub. Date: Jun. 5, 2003

(65) Prior Publication Data

US 2004/0247482 A1 Dec. 9, 2004

(30) Foreign Application Priority Data

Nov. 26, 2001 (SE) .................................... 0103937

(51) Int. Cl.
*A61L 2/00* (2006.01)
*A61L 2/18* (2006.01)
*A61L 9/00* (2006.01)

(52) U.S. Cl. ............................... 422/28; 422/24; 422/31

(58) Field of Classification Search .................... 422/31, 422/298, 20, 28; 239/102.2
See application file for complete search history.

(56) References Cited

U.S. PATENT DOCUMENTS 3,281,859 A * 10/1966 Stone ........................... 347/75
4,175,266 A * 11/1979 Nakano et al. ................. 347/77
4,281,329 A * 7/1981 Yano et al. .................... 347/100
4,361,400 A * 11/1982 Gray et al. ..................... 256/23
4,591,485 A * 5/1986 Olsen et al. .................... 422/20

(Continued)

FOREIGN PATENT DOCUMENTS

DE 4209838 A1 9/1993

(Continued)

*Primary Examiner*—E. Leigh McKane
*Assistant Examiner*—Regina Yoo
(74) *Attorney, Agent, or Firm*—Buchanan Ingersoll & Rooney PC

(57) ABSTRACT

Method of sterilising a packaging material (1) by means of a sterilising agent in liquid form, comprising the steps of: providing a packaging material (1) to be sterilised, providing a source (11) of sterilising agent in liquid form, forcing the liquid sterilising agent through a nozzle (12) to form a jet (14*a*) directed towards the packaging material, subjecting the jet (14*a*) of liquid sterilising agent to a controlled, periodic disturbance causing the jet (14*a*) of liquid sterilising agent to form a train (14) of droplets of controlled, essentially uniform size and controlled rate, moving the packaging material (1) in relation to said nozzle (12) or vice versa, whereby said train (14) of droplets forms a coating (2) of sterilising agent of controlled thickness and controlled coverage on the packaging material (1), and vaporising the film of sterilising agent on the packaging material (1). The invention also concerns a similar method and devices for implementing said methods.

7 Claims, 2 Drawing Sheets

U.S. PATENT DOCUMENTS

| | | | | |
|---|---|---|---|---|
| 4,680,163 | A * | 7/1987 | Blidschun et al. | 422/28 |
| 4,707,334 | A * | 11/1987 | Gerhard | 422/28 |
| 5,364,590 | A * | 11/1994 | Hillebrenner | 422/28 |
| 5,424,034 | A * | 6/1995 | Hilmersson | 422/28 |
| 5,560,543 | A * | 10/1996 | Smith et al. | 239/102.2 |
| 5,641,457 | A * | 6/1997 | Vardanega et al. | 422/82.01 |
| 5,736,195 | A * | 4/1998 | Haaland | 427/180 |
| 5,763,170 | A * | 6/1998 | Raybuck | 435/6 |
| 5,810,988 | A * | 9/1998 | Smith et al. | 204/666 |
| 5,843,374 | A * | 12/1998 | Sizer et al. | 422/24 |
| 5,882,591 | A * | 3/1999 | Kekez | 422/28 |
| 6,027,699 | A * | 2/2000 | Holcomb et al. | 422/186.04 |
| 6,056,918 | A * | 5/2000 | Palaniappan et al. | 422/24 |
| 6,242,764 | B1 | 6/2001 | Ohba et al. | |
| 6,266,355 | B1 | 7/2001 | Sverdlov | |
| 6,379,427 | B1 * | 4/2002 | Siess | 95/57 |
| 6,379,616 | B1 * | 4/2002 | Sheiman | 422/31 |
| 6,488,753 | B1 * | 12/2002 | Ito et al. | 106/31.9 |
| 6,657,237 | B2 | 12/2003 | Chae et al. | |
| 6,706,243 | B1 * | 3/2004 | Sias et al. | 422/28 |
| 6,746,652 | B2 * | 6/2004 | Khorzad et al. | 422/305 |
| 6,969,487 | B1 * | 11/2005 | Sias et al. | 422/28 |
| 7,008,592 | B2 * | 3/2006 | Sias et al. | 422/28 |
| 7,090,808 | B2 * | 8/2006 | Caputo et al. | 422/305 |
| 2001/0006235 | A1 * | 7/2001 | Ozawa | 257/79 |
| 2002/0085971 | A1 * | 7/2002 | Raniwala | 422/303 |
| 2002/0197184 | A1 * | 12/2002 | Palaniappan | 422/22 |
| 2003/0057294 | A1 * | 3/2003 | Bank et al. | 239/102.2 |
| 2005/0025665 | A1 * | 2/2005 | Raniwala | 422/28 |

FOREIGN PATENT DOCUMENTS

| | | | |
|---|---|---|---|
| EP | 0484730 | B1 | 5/1992 |
| EP | 0484730 | B1 * | 2/1995 |
| GB | 2089213 | A * | 6/1982 |
| GB | 2089213 | A | 6/1982 |
| WO | 0137886 | A1 | 5/2001 |

* cited by examiner

US 7,604,773 B2

METHOD OF STERILISING A PACKAGING MATERIAL BY MEANS OF A STERILISING AGENT IN LIQUID FORM

TECHNICAL FIELD

The present invention concerns a method of and device for sterilising a packaging material by means of a sterilising agent in liquid form.

TECHNICAL BACKGROUND

Aseptic packaging technology has for a long time been used for packaging foodstuffs and the like, especially products sensitive to bacteria and storage, in order to give the product an extended shelf life so that it can be retained for longer periods of time from the day of packaging without risk of being spoiled or deteriorating. The technology is well known to an artisan and can for example start out from the fact that the product and the packaging material are each subjected to a sterilising treatment for the purpose of neutralising harmful micro-organisms occurring in the product of the packaging material, and that the treated product is thereafter enclosed in the sterilised packaging material under sterile conditions in order to avoid a bacterial reinfection of the sterilised product.

Aseptic packagings for milk, juice and similar liquid foods are now most frequently produced with the aid of packaging machines of the type that, from a strip or sheet of plastic coated paper or cardboard material, forms, fills and closes packages under aseptic conditions. From, for example, in a known packaging machine that produces aseptic packagings for milk, the strip is led through a bath containing 10-35% by weight of hydrogen peroxide within a chamber essentially completely screened from the environment. After the passage through the bath the strip is pinched between press rollers in order to remove the surplus sterilising agent from the strip and return it to the bath.

Thereafter the strip, without coming into contact with the machine environment is led into the forming and filling chamber of the machine, which chamber is likewise essentially completely screened from the environment. In the forming and filling chamber, the packaging material is heated by means for sterile hot air in order to vaporise and drive away the residue of accompanying sterilising agent from the packaging material, whereby the strip is shaped into a tube by sealing the two longitudinal edges to each other in a longitudinal overlap joint. The tube is filled with the appropriate previously sterilised contents, heat treated milk or the like, which is fed to the tube through a filler pipe opening into the tube, and separated into closed, filled packagings through repeated transverse sealings of the tube across the longitudinal axis of the tube.

The packagings are separated from each other through cuts in the transverse sealings and are subsequently given the desired geometric final shape, usually of parallelepipedic type, before out feed of the finished aseptic packagings from the machine. During the whole process an overpressure of sterile hot air is maintained in the shaping and filling chamber in order to prevent unsterile environmental air from penetrating and reinfecting the sterilised contents and the packaging material.

A precondition for achieving good sterilisation of the packaging material in the above-described known method is that the whole strip, after passing through the sterilising bath, is covered by a coherent film of sterilising agent in order to ensure that all parts of the packaging material are effectively sterilised. The film should in addition preferably be thin and of even thickness in order to facilitate and make more effective the subsequent vaporisation of the sterilising agent in the shaping and filling chamber. These two conditions have been shown difficult to fulfil in practice and it not infrequently happens that the sterilising agent exhibits an irregular film thickness over the strip surface, which not only leads to an uneven and unpredictable sterilisation effect but also makes the vaporisation more difficult.

Another disadvantage with the above described and other known methods, which employ a bath of sterilising agent through which the strip is trained, is the edge suction phenomenon which entails that the exposed fibrous material in the longitudinal cut edges have a tendency to absorb the liquid sterilising agent which is retained in the fibrous layer of the strip. Since the inward facing cut edges in the finished packagings are always well protected no risk occurs that accompanying sterilising agent should come in contact with and affect the contents of the packaging, but on the contrary the risk is great that the liquid absorbed will at least locally cause deterioration in the rigidity and stability of form of the packaging at the same time as it of course entails an unnecessary loss of sterilising agent.

Another problem associated with this type of sterilising method occurs when the sterilising method is applied to packaging materials including pre-applied opening devices. The pre-applied openings act as shovels or bailers transporting considerable amounts of sterilising agent from the bath. Due to the conventional shape of the opening devices the above-mentioned press rollers are not able to prevent this phenomenon from occurring.

EP 484730 A1 discloses a method of sterilising a packaging material by means of a sterilising agent in a liquid form. The packaging material is discharged in order to eliminate the electrostatic surface charges on the packaging material. Thereafter the packaging material is wetted with the sterilising agent, which is applied in as a finely distributed, electrostatically charged, mist to those areas of the packaging material that are to be sterilised. The packaging material with the sterilising agent, which has coalesced to a thin film, is finally heated to vaporize the sterilising agent from the ready sterilised packaging material. EP 484730 A1 is presently considered closest prior art.

However, this method also suffers some drawbacks; it is hard to properly discharge the packaging material since the training of the packaging material around bending rolls, forming rolls, etc induces quite a lot electrostatic charge of the packaging material. Furthermore, the mist of sterilising agent does not result in an even film on the packaging material.

SUMMARY OF INVENTION

Thus, it is an object of the invention to provide a method and device for sterilising a packaging material by means of a sterilising agent in liquid form by which the sterilising agent is applied in a consistent and controlled manner, the package is not subjected to edge suction and by which the sterilising agent is utilised without any excessive losses due to the pre-applied opening devices.

This and further objects that will be apparent by the following description are achieved by a method comprising the steps of providing a packaging material to be sterilised, providing a source of sterilising agent in liquid form, forcing the liquid sterilising agent through a nozzle to form a jet directed towards the packaging material, subjecting the jet of liquid sterilising agent to a controlled, periodic disturbance causing the jet of liquid sterilising agent to form a train of droplets of controlled, essentially uniform size and controlled rate, moving the packaging material in relation to said nozzle or vice versa, whereby said train of droplets forms a coating of sterilising agent of controlled thickness and controlled coverage on the packaging material, and vaporising the film of sterilising agent on the packaging material. This method has amongst others, in comparison with the prior art methods described above, the advantages of controlled delivery of a sterilising agent (e g hydrogen peroxide) in terms of film thickness/mass, temperature and location.

When scrutinizing the method described in EP 484730 A1 it has been found that, even though the droplets in the mist at first sight seems to be evenly distributed and the effect of spreading the droplets onto a wider area at first sight seems to introduce some kind of redundancy to the method, the droplets in the mist is not evenly distributed at all. This implies that the film created by the mist has at best an uneven thickness, but even worse it in many cases is not a continuous film even if so desired.

It is known that forcing a liquid through an orifice or nozzle creates a jet. As the jet leaves the nozzle random disturbances will occur on the surface of the jet. These disturbances, together with an inherent strive to minimise the surface tension for the free flowing jet, desire to minimise the surface energy, which cause the jet to break-up into droplets. This natural mechanism gives a random distribution of droplet sizes and droplet formation rates. Furthermore, it gives rise to a random distribution in the direction of the droplets. Due to the random nature of the prior art method, the sterilising agent must be supplied in an amount large enough to make certain that even the portions of the packaging material receiving the smallest amount of the sterilising agent receive enough sterilising agent.

By the inventive method the random break-up is overridden by the controlled, periodic disturbances, which leads to the advantages as described above. The source of external disturbance is often a piezoelectric crystal but can be some other device that vibrates the nozzle. Electrical stimulation of the crystal causes mechanical vibrations that are introduced to the jet. The frequency of the stimulation signal affects the droplet size and the difference between droplets, while the amplitude influences the distance from the nozzle to the point where the jet breaks up.

The droplet size depends not only on the stimulation frequency but also on the nozzle design and the properties of the liquid. The nozzle design affects the hydrodynamic conditions, the pressure drop etc in nozzle—good design can give enhanced flow. It is also important to consider the viscosity of the liquid; as the viscosity decreases with temperature a higher temperature of the liquid enables consequently higher ejection rates.

Another difference is that these controlled disturbances make it possible to get a train of droplets essentially along a single imaginary line instead of the random distribution of the direction of the droplets as in the prior art method. This makes it possible to in a controlled manner get different amounts of sterilising agent on different portions of the packaging material. This can e.g. be of interest when the packaging material is provided with pre-applied opening devices.

According to an embodiment of the invention, the droplets are electrically charged and deflection electrodes will deflect either the wanted or the unwanted droplets. The unwanted droplets are gathered in a gutter of some kind and preferably returned to the source of sterilising agent or to the nozzle.

Of course the packaging material in question could be roll-fed with or without pre-applied openings, it could be more or less erected blanks or any other configuration of semi-finished packagings.

Above mentioned objects are also achieved by a method wherein the above mentioned steps of forcing and subjecting is made in a single step; namely by forcing the liquid sterilising agent through a nozzle to form a train of droplets of controlled, essentially uniform size and controlled rate, travelling in a direction towards the packaging material, by subjecting the liquid in said source to a controlled disturbance whenever a droplet is desired. The advantages of the method as such have been mentioned above in relation to the above-described method. This aspect of the invention is as such adapted to be able to apply different amounts of sterilising agent on different portions of the packaging material since the droplets are only created when desired. The train of droplets could also be an intermittent jet with a length and volume corresponding to the volume of a number of droplets.

Preferably, the sterilising agent on the packaging material is vaporised by applying heat to the sterilising agent on the packaging material.

Preferably, the nozzle is arranged in an array including a plurality of nozzles, whereby the array is moving in relation to the packaging material or vice versa to and fro between a first position and a second position. If a continuous film is wanted and the redundancy should be complete in respect of a failure of a single nozzle, the distance between the first and second position should be at least the distance between two nozzles that are adjacent to each other in respect of distance in direction perpendicular to the direction of travel of the packaging material. The redundancy can also, alone or in combination with the movement of the array be accomplished by arrangement of more than one nozzle in the direction of relative travel of the packaging material in relation to the array of nozzles. Of course, the exact arrangement and numbers of nozzles in the array as well as the movement of the array must be considered and optimised in respective case. Among others one must take into account the reliability of each nozzle, the need of continuous film or not, the speed of travel of the packaging material, etc. Dependent on the different values on these and other parameters, it in some cases might be advantageous to use many more or less fixed nozzles, while it in other cases might be more advantageous to use fewer nozzles and instead move the array of nozzles more.

According to a preferred embodiment the sterilising of the packaging material with the liquid sterilising agent is supplemented with a step of subjecting the packaging material to radiation, preferably UV-radiation. The supplemental radiation sterilising makes it possible to use less sterilising agent further enhancing the advantages mentioned above.

The objects of the invention have also been achieved with a device as set out in the independent device claims. The advantages achieved have been discussed in relation to the method. Preferred embodiments are described in the dependent claims.

BRIEF DESCRIPTION OF THE DRAWINGS

The invention will be described in more detail with reference to the appended schematic drawings, which shows examples of presently preferred embodiments of the invention.

DETAILED DESCRIPTION OF PREFERRED EMBODIMENTS

Figure 1:
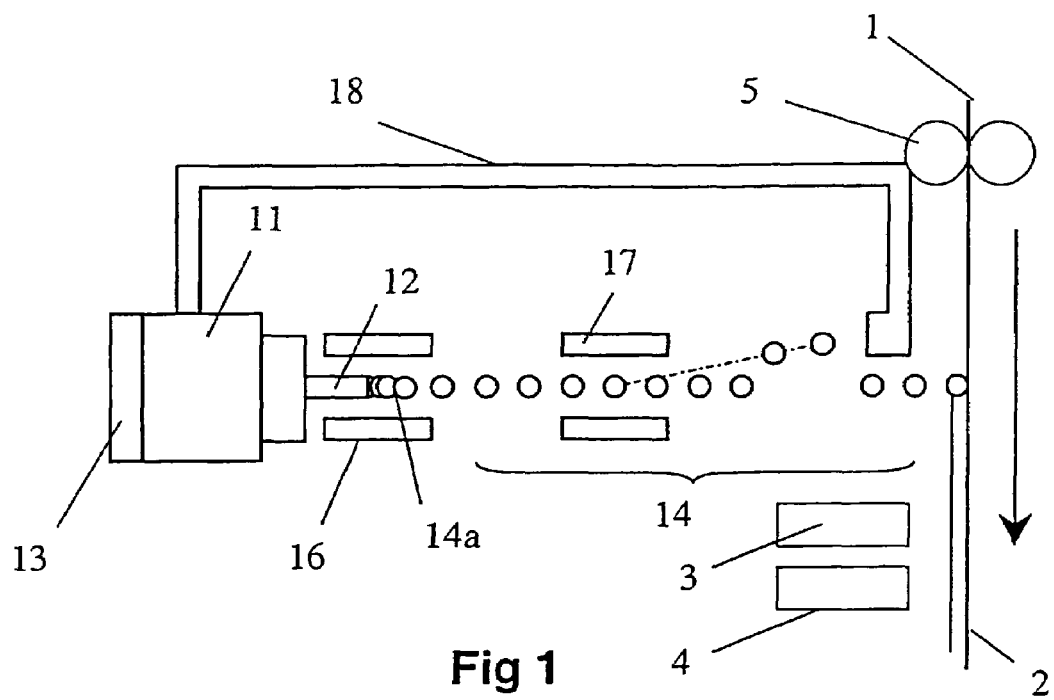
FIG. 1 is a side view of a device implementing the continuous method.
Figure 2:
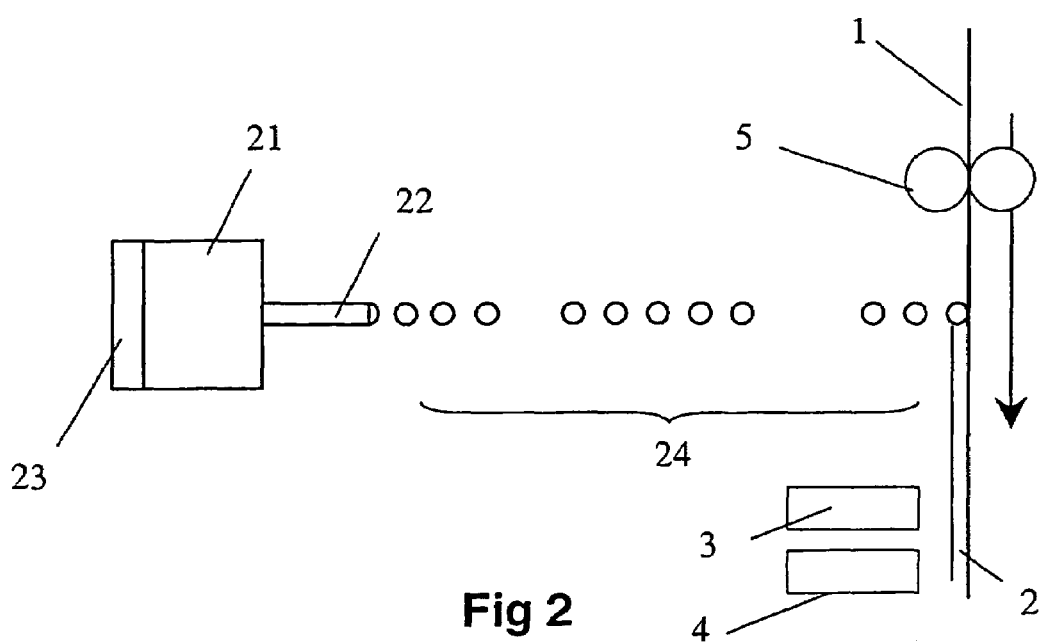
FIG. 2 is a side view of a device implementing the on-demand method.
Figure 3:
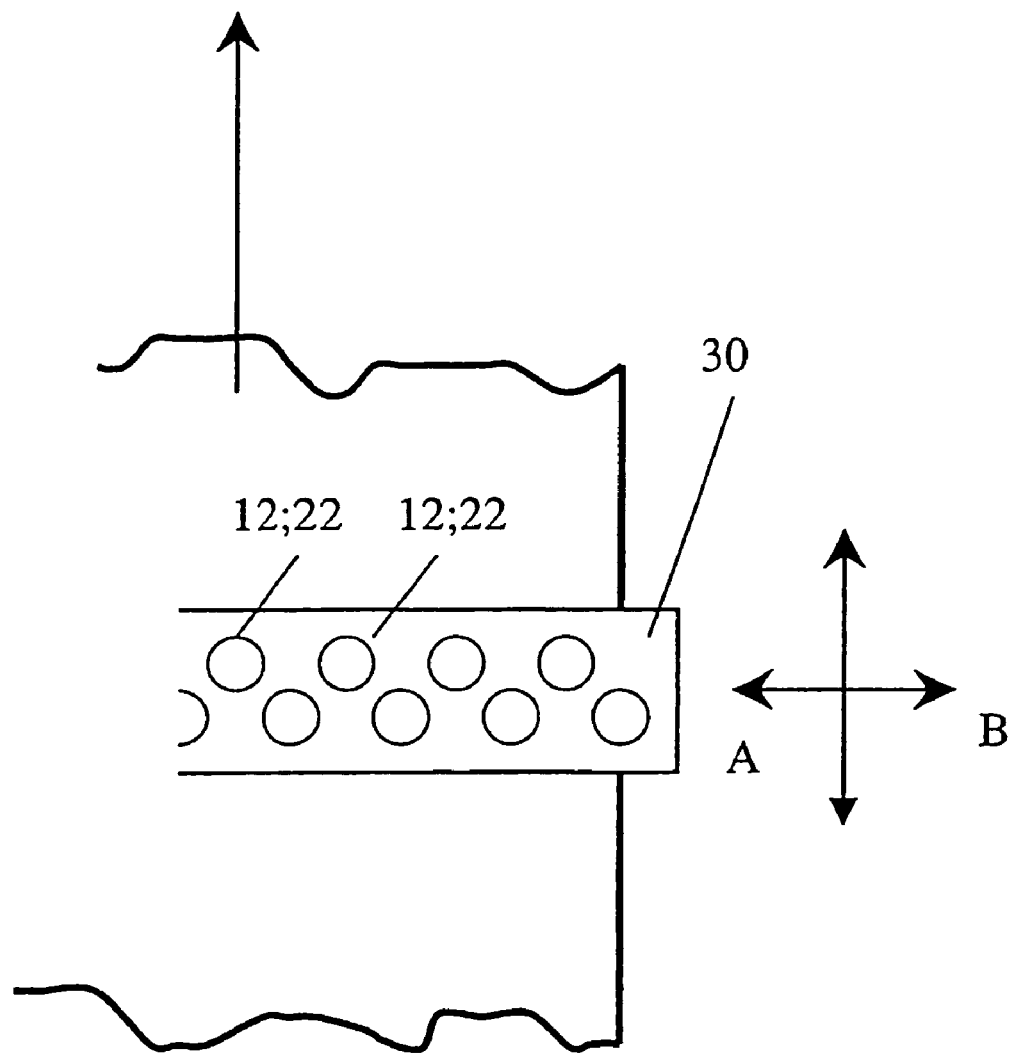
FIG. 3 is a plan view showing an array of nozzles.

There are mainly two different technologies to achieve the above-mentioned train of droplets of controlled, essentially uniform size and controlled rate; namely the continuous and the on-demand technology.

The device according to both aspects comprises a source 11, 21 of sterilising agent, a nozzle 12, 22, and means 13, 23 for pressurising the sterilising agent.

In accordance with the continuous method the pressurising means 13, such as a membrane, forces a liquid sterilising agent through a nozzle 12 to form a jet 14a directed towards the packaging material, the jet being subjected to a controlled, periodic disturbance causing the jet of liquid sterilising agent to form a train 14 of droplets of controlled, essentially uniform size and controlled rate. The stimulation source is usually a piezoelectric crystal vibrating at high frequency, but of course can other means accomplishing similar vibrations be used. The sterilising agent is normally electrically discharged by connection to earth. The packaging material 1 is moved in relation to the nozzle (for example by a driving means 5) or vice versa, whereby the train of droplets forms a coating 2 of sterilising agent of controlled thickness and controlled coverage on the packaging material. The film of sterilising agent on the packaging material can be vaporized (for example by a heating means 3). The sterilising of the packaging material 1 with the liquid sterilising agent can be supplemented by subjecting the packaging material to radiation from a radiation source 4, preferably UV-radiation.

If for some reason certain parts of the packaging material are not to be provided with the sterilising agent at all or in an amount differing from the rest of the packaging material this can be achieved by a technology where the droplets are electrically charged with charging electrodes 16 and deflection electrodes 17 will, depending on technique version, deflect either the wanted or the unwanted droplets. The unwanted droplets are returned via a gutter 18. Thus, in the continuous technology this last step of control of the location and rate of location relies on that the droplets can be electrically charged.

Typical data for continuous methods: Frequencies of the stimulation source: 50 000 to 150 000 Hz (in some cases up to 1 MHz); Droplet sizes 100-400 micrometers (in some cases down to 10-15 micrometers).

In accordance with the on-demand or impulse technology, the liquid sterilising agent is forced through a nozzle 22 to form a train 24 of droplets of controlled, essentially uniform size and controlled rate, travelling in a direction towards the packaging material 1, by subjecting the liquid in said source to a controlled disturbance whenever a droplet is desired. Thus, in the drop-on-demand technology, droplets or intermittent jets with a volume corresponding to a few droplets are generated only when needed. In the so-called thermal or bubble jet version, the stimulation source 23 is a resistor (resistive heating element) that, when electrically stimulated, heats the liquid and thus causes liquid expansion. A vapour bubble is created and the resulting pressure wave forces an equivalent volume of liquid through the nozzle. Also some drop-on-demand techniques make use of a piezoelectric crystal 23. Others make use of an electrode 23 as the stimulation source.

In impulse ink jet technology, deflection of droplets is not needed, and consequently these techniques do not rely on any electrical charging of the liquid to control the impact variation over time. Typical data for impulse methods; Frequencies of the stimulation source: 500 to 12 000 Hz; Droplet sizes approximate range 30-500 micrometers.

Preferably, the nozzle 12, 22 is arranged in an array 30 including a plurality of nozzles, whereby the array 30 is moving in relation to the packaging material or vice versa to and fro between a first position A and a second position B.

It should be noted that several modifications of the described preferred embodiments is possible within the scope of the invention as defined in the claims.

The sterilising agent could be for example a hydrogen peroxide solution or any other sterilisation chemical. Preferably a hydrogen peroxide water solution with a few up to 40 weight percent hydrogen peroxide is used.

The stimulation source could also be a vibrating membrane or any similar device that can transfer a vibration into the liquid sterilising agent or to the nozzle.

The invention claimed is:

1. Method of sterilising a packaging material, comprising
    forcing liquid hydrogen peroxide as a sterilising agent through a nozzle to form a jet directed towards a packaging material,
    subjecting the jet of liquid hydrogen peroxide to a controlled, periodic disturbance causing the jet of liquid hydrogen peroxide to form a train of hydrogen peroxide droplets substantially along a single imaginary line and of controlled, essentially uniform size and controlled rate,
    electrically charging the hydrogen peroxide droplets to produce electrically charged hydrogen peroxide droplets by conveying the hydrogen peroxide droplets between two charging plates,
    deflecting either wanted or unwanted hydrogen peroxide droplets by conveying the electrically charged hydrogen peroxide droplets between a pair of deflection plates,
    moving the packaging material in relation to said nozzle or vice versa, so that the wanted hydrogen peroxide droplets are applied to the packaging material to form a coating of hydrogen peroxide of controlled thickness and controlled coverage on the packaging material, and
    vaporising the film of hydrogen peroxide on the packaging material to carry out sterilisation of the packaging material.

2. Method according to claim 1, wherein the film of hydrogen peroxide is vaporised by applying heat to the hydrogen peroxide on the packaging material.

3. Method according to claim 1, wherein the train of droplets form an essentially continuous film.

4. Method according to claim 1, wherein the nozzle is arranged in an array including a plurality of nozzles, the array being moved in relation to the packaging material or vice versa between a first position and a second position.

5. Method according to claim 1, further comprising subjecting the packaging material to radiation.

6. Method according to claim 5, wherein the radiation is UV radiation.

7. Method according to claim 1, wherein the jet of liquid hydrogen peroxide is subjected to mechanical vibrations to cause the controlled, periodic disturbance.

\* \* \* \* \*